(12) United States Patent
Alamin et al.

(10) Patent No.: US 8,162,982 B2
(45) Date of Patent: Apr. 24, 2012

(54) METHODS AND SYSTEMS FOR CONSTRAINT OF MULTIPLE SPINE SEGMENTS

(75) Inventors: Todd Alamin, Woodside, CA (US); Ian Bennett, San Francisco, CA (US); Louis Fielding, San Carlos, CA (US); Colin Cahill, San Francisco, CA (US)

(73) Assignee: Simpirica Spine, Inc., San Carlos, CA (US)

( * ) Notice: Subject to any disclaimer, the term of this patent is extended or adjusted under 35 U.S.C. 154(b) by 232 days.

(21) Appl. No.: 12/426,119

(22) Filed: Apr. 17, 2009

(65) Prior Publication Data

US 2009/0264932 A1   Oct. 22, 2009

Related U.S. Application Data

(63) Continuation-in-part of application No. PCT/US2007/081822, filed on Oct. 18, 2007.

(60) Provisional application No. 60/862,085, filed on Oct. 19, 2006.

(51) Int. Cl.
*A61B 17/70* (2006.01)
(52) U.S. Cl. ...................................... 606/248
(58) Field of Classification Search ........... 606/246–279
See application file for complete search history.

(56) References Cited

U.S. PATENT DOCUMENTS

| | | |
|---|---|---|
| 3,648,691 A | 3/1972 | Lumb et al. |
| 4,246,660 A | 1/1981 | Wevers |
| 4,643,178 A | 2/1987 | Nastari et al. |
| 4,708,132 A | 11/1987 | Silvestrini |
| 4,743,260 A | 5/1988 | Burton |
| 4,772,286 A | 9/1988 | Goble et al. |
| 4,776,851 A | 10/1988 | Bruchman et al. |
| 4,794,916 A | 1/1989 | Porterfield et al. |
| 4,870,957 A | 10/1989 | Goble et al. |
| 4,955,910 A | 9/1990 | Bolesky |
| 4,966,600 A | 10/1990 | Songer et al. |
| 5,002,574 A | 3/1991 | May et al. |
| 5,011,484 A * | 4/1991 | Breard .......................... 606/249 |
| 5,011,494 A | 4/1991 | von Recum et al. |

(Continued)

FOREIGN PATENT DOCUMENTS

EP   0 322 334 A1   6/1989

(Continued)

OTHER PUBLICATIONS

Al Baz et al., "Modified Technique of Tension Band Wiring in Flexion Injuries of the Middle and Lower Cervical Spine," Spine, vol. 20, No. 11, 1995, p. 1241-1244.

(Continued)

*Primary Examiner* — Eduardo C Robert
*Assistant Examiner* — David Comstock
(74) *Attorney, Agent, or Firm* — Wilson Sonsini Goodrich & Rosati

(57) ABSTRACT

Methods, apparatus and systems for constraining spinous processes to elastically limit flexion of two or more adjacent spinal segments rely on placing a tether structure over at least three adjacent vertebral bodies or two adjacent vertebral bodies and the sacrum. The tether structures may be continuous, for example in the form of a continuous loop, or may be discontinuous, for example in the form of a loop or elongate element having at least two anchor structures for securing in bone.

9 Claims, 7 Drawing Sheets

U.S. PATENT DOCUMENTS

| | | |
|---|---|---|
| 5,030,220 A | 7/1991 | Howland |
| 5,092,866 A | 3/1992 | Breard et al. |
| 5,108,433 A | 4/1992 | May et al. |
| 5,116,340 A | 5/1992 | Songer et al. |
| 5,171,280 A | 12/1992 | Baumgartner |
| 5,180,393 A | 1/1993 | Commarmond |
| 5,282,863 A | 2/1994 | Burton |
| 5,354,917 A | 10/1994 | Sanderson et al. |
| 5,366,455 A | 11/1994 | Dove et al. |
| 5,387,213 A * | 2/1995 | Breard et al. ............. 606/254 |
| 5,395,374 A | 3/1995 | Miller et al. |
| 5,415,658 A | 5/1995 | Kilpela et al. |
| 5,415,661 A | 5/1995 | Holmes |
| 5,449,361 A | 9/1995 | Preissman |
| 5,456,722 A | 10/1995 | McLeod et al. |
| 5,458,601 A | 10/1995 | Young, Jr. et al. |
| 5,462,542 A | 10/1995 | Alesi, Jr. |
| 5,496,318 A | 3/1996 | Howland et al. |
| 5,540,698 A | 7/1996 | Preissman |
| 5,562,737 A | 10/1996 | Graf |
| 5,593,407 A | 1/1997 | Reis |
| 5,609,634 A * | 3/1997 | Voydeville ............. 623/13.11 |
| 5,628,756 A | 5/1997 | Barker, Jr. et al. |
| 5,645,084 A | 7/1997 | McKay |
| 5,645,599 A | 7/1997 | Samani |
| 5,669,917 A | 9/1997 | Sauer et al. |
| 5,672,175 A | 9/1997 | Martin |
| 5,707,379 A | 1/1998 | Fleenor et al. |
| 5,725,582 A * | 3/1998 | Bevan et al. ............. 606/263 |
| 5,810,815 A | 9/1998 | Morales |
| 5,836,948 A | 11/1998 | Zucherman et al. |
| 5,902,305 A | 5/1999 | Beger et al. |
| RE36,221 E | 6/1999 | Breard et al. |
| 5,928,232 A | 7/1999 | Howland et al. |
| 5,933,452 A | 8/1999 | Eun |
| 5,935,133 A | 8/1999 | Wagner et al. |
| 5,964,769 A | 10/1999 | Wagner et al. |
| 5,989,256 A | 11/1999 | Kuslich et al. |
| 6,053,921 A | 4/2000 | Wagner et al. |
| 6,193,721 B1 | 2/2001 | Michelson |
| 6,224,630 B1 | 5/2001 | Bao et al. |
| 6,248,106 B1 | 6/2001 | Ferree |
| 6,283,996 B1 | 9/2001 | Chervitz et al. |
| 6,287,308 B1 | 9/2001 | Betz et al. |
| 6,290,724 B1 | 9/2001 | Marino |
| 6,296,643 B1 | 10/2001 | Hopf et al. |
| 6,312,431 B1 | 11/2001 | Asfora |
| 6,322,279 B1 | 11/2001 | Yamamoto et al. |
| 6,364,883 B1 * | 4/2002 | Santilli ............. 606/279 |
| 6,378,289 B1 | 4/2002 | Trudeau et al. |
| 6,391,030 B1 | 5/2002 | Wagner et al. |
| 6,395,018 B1 | 5/2002 | Castaneda |
| 6,427,080 B1 | 7/2002 | Radak |
| 6,436,099 B1 | 8/2002 | Drewry et al. |
| 6,451,019 B1 | 9/2002 | Zucherman et al. |
| 6,468,309 B1 | 10/2002 | Lieberman |
| 6,517,578 B2 | 2/2003 | Hein |
| 6,558,389 B2 | 5/2003 | Clark et al. |
| 6,582,433 B2 | 6/2003 | Yun |
| 6,589,246 B1 | 7/2003 | Hack et al. |
| 6,605,091 B1 | 8/2003 | Iwanski |
| 6,616,669 B2 | 9/2003 | Ogilvie et al. |
| 6,626,944 B1 | 9/2003 | Taylor |
| 6,629,975 B1 | 10/2003 | Kilpela et al. |
| 6,652,527 B2 | 11/2003 | Zucherman et al. |
| 6,652,585 B2 | 11/2003 | Lange |
| 6,656,185 B2 * | 12/2003 | Gleason et al. ............. 606/74 |
| 6,669,729 B2 | 12/2003 | Chin |
| 6,682,533 B1 | 1/2004 | Dinsdale et al. |
| 6,689,140 B2 | 2/2004 | Cohen |
| 6,689,168 B2 | 2/2004 | Lieberman |
| 6,695,852 B2 | 2/2004 | Gleason |
| 6,712,819 B2 | 3/2004 | Zucherman et al. |
| 6,716,245 B2 | 4/2004 | Pasquet et al. |
| 6,761,720 B1 | 7/2004 | Senegas |
| 6,828,357 B1 | 12/2004 | Martin et al. |
| 6,835,205 B2 | 12/2004 | Atkinson et al. |
| 6,899,716 B2 | 5/2005 | Cragg et al. |
| 6,989,011 B2 | 1/2006 | Paul et al. |
| 7,029,475 B2 | 4/2006 | Panjabi |
| 7,163,558 B2 | 1/2007 | Senegas et al. |
| 7,201,751 B2 | 4/2007 | Zucherman et al. |
| 7,335,203 B2 * | 2/2008 | Winslow et al. ............. 606/249 |
| 7,413,576 B2 | 8/2008 | Sybert et al. |
| 7,452,351 B2 | 11/2008 | Miller et al. |
| 7,458,981 B2 | 12/2008 | Fielding et al. |
| 7,520,887 B2 | 4/2009 | Maxy et al. |
| 7,524,324 B2 | 4/2009 | Winslow |
| 7,553,320 B2 | 6/2009 | Molz, IV et al. |
| 7,591,837 B2 | 9/2009 | Goldsmith |
| 7,909,853 B2 | 3/2011 | Zucherman et al. |
| 8,029,549 B2 | 10/2011 | Malandain et al. |
| 2001/0007073 A1 | 7/2001 | Zucherman et al. |
| 2002/0095154 A1 * | 7/2002 | Atkinson et al. ............. 606/61 |
| 2002/0147449 A1 * | 10/2002 | Yun ............. 606/61 |
| 2002/0151978 A1 | 10/2002 | Zacouto et al. |
| 2002/0161446 A1 | 10/2002 | Bryan et al. |
| 2003/0023241 A1 | 1/2003 | Drewry et al. |
| 2003/0050700 A1 | 3/2003 | Kihara |
| 2003/0088251 A1 | 5/2003 | Braun et al. |
| 2004/0024458 A1 | 2/2004 | Senegas et al. |
| 2004/0034351 A1 * | 2/2004 | Sherman et al. ............. 606/61 |
| 2004/0082954 A1 | 4/2004 | Teitelbaum et al. |
| 2004/0106995 A1 | 6/2004 | Le Couedic et al. |
| 2004/0116927 A1 | 6/2004 | Graf |
| 2004/0117017 A1 | 6/2004 | Pasquet et al. |
| 2004/0127989 A1 | 7/2004 | Dooris et al. |
| 2004/0143268 A1 | 7/2004 | Falahee |
| 2004/0167520 A1 | 8/2004 | Zucherman et al. |
| 2004/0172132 A1 | 9/2004 | Ginn |
| 2004/0215341 A1 * | 10/2004 | Sybert et al. ............. 623/13.17 |
| 2004/0243239 A1 | 12/2004 | Taylor |
| 2005/0033435 A1 | 2/2005 | Belliard et al. |
| 2005/0049708 A1 | 3/2005 | Atkinson et al. |
| 2005/0123581 A1 | 6/2005 | Ringeisen et al. |
| 2005/0131405 A1 | 6/2005 | Molz, IV et al. |
| 2005/0154390 A1 | 7/2005 | Biedermann et al. |
| 2005/0192581 A1 * | 9/2005 | Molz et al. ............. 606/74 |
| 2005/0203624 A1 | 9/2005 | Serhan et al. |
| 2005/0216017 A1 | 9/2005 | Fielding et al. |
| 2005/0228383 A1 | 10/2005 | Zucherman et al. |
| 2005/0267470 A1 | 12/2005 | McBride |
| 2005/0267518 A1 | 12/2005 | Wright et al. |
| 2006/0036324 A1 | 2/2006 | Sachs et al. |
| 2006/0041259 A1 | 2/2006 | Paul et al. |
| 2006/0064166 A1 | 3/2006 | Zucherman et al. |
| 2006/0069447 A1 | 3/2006 | DiSilvestro et al. |
| 2006/0084976 A1 | 4/2006 | Borgstrom et al. |
| 2006/0106381 A1 | 5/2006 | Ferree et al. |
| 2006/0106397 A1 | 5/2006 | Lins |
| 2006/0136060 A1 | 6/2006 | Taylor |
| 2006/0142760 A1 | 6/2006 | McDonnell |
| 2006/0149230 A1 | 7/2006 | Kwak et al. |
| 2006/0195102 A1 | 8/2006 | Malandain |
| 2006/0217726 A1 | 9/2006 | Maxy et al. |
| 2006/0240533 A1 | 10/2006 | Sengupta et al. |
| 2006/0241610 A1 | 10/2006 | Lim et al. |
| 2006/0271055 A1 | 11/2006 | Thramann |
| 2007/0010822 A1 | 1/2007 | Zalenski et al. |
| 2007/0073293 A1 | 3/2007 | Martz et al. |
| 2007/0083200 A1 | 4/2007 | Gittings et al. |
| 2007/0173818 A1 * | 7/2007 | Hestad et al. ............. 606/61 |
| 2007/0213829 A1 | 9/2007 | Le Couedic et al. |
| 2007/0233096 A1 | 10/2007 | Garcia-Bengochea |
| 2007/0270828 A1 * | 11/2007 | Bruneau et al. ............. 606/61 |
| 2007/0299445 A1 | 12/2007 | Shadduck et al. |
| 2008/0009866 A1 | 1/2008 | Alamin et al. |
| 2008/0021466 A1 | 1/2008 | Shadduck et al. |
| 2008/0027435 A1 | 1/2008 | Zucherman et al. |
| 2008/0033552 A1 | 2/2008 | Lee et al. |
| 2008/0045949 A1 | 2/2008 | Hunt et al. |
| 2008/0051784 A1 | 2/2008 | Gollogly |
| 2008/0097431 A1 | 4/2008 | Vessa |
| 2008/0108993 A1 | 5/2008 | Bennett et al. |
| 2008/0114357 A1 | 5/2008 | Allard et al. |
| 2008/0125780 A1 | 5/2008 | Ferree |
| 2008/0177264 A1 | 7/2008 | Alamin et al. |

| | | | |
|---|---|---|---|
| 2008/0177298 | A1 | 7/2008 | Zucherman et al. |
| 2008/0183209 | A1 | 7/2008 | Robinson et al. |
| 2008/0262549 | A1 | 10/2008 | Bennett et al. |
| 2008/0281423 | A1 | 11/2008 | Sheffer et al. |
| 2008/0312693 | A1 | 12/2008 | Trautwein et al. |
| 2008/0319487 | A1 | 12/2008 | Fielding et al. |
| 2009/0030457 | A1 | 1/2009 | Janowski et al. |
| 2009/0082820 | A1 | 3/2009 | Fielding et al. |
| 2009/0118766 | A1 | 5/2009 | Park et al. |
| 2009/0182296 | A1 | 7/2009 | Fielding et al. |
| 2009/0198282 | A1 | 8/2009 | Fielding et al. |
| 2009/0264929 | A1 | 10/2009 | Alamin et al. |
| 2009/0270918 | A1 | 10/2009 | Attia et al. |
| 2010/0004701 | A1 | 1/2010 | Malandain et al. |
| 2010/0023060 | A1 | 1/2010 | Bennett et al. |
| 2010/0036424 | A1 | 2/2010 | Fielding et al. |
| 2010/0234890 | A1 | 9/2010 | Alamin et al. |
| 2010/0234894 | A1 | 9/2010 | Alamin et al. |
| 2010/0249839 | A1 | 9/2010 | Alamin et al. |

FOREIGN PATENT DOCUMENTS

| | | |
|---|---|---|
| EP | 0 743 045 A2 | 11/1996 |
| EP | 0743045 A3 | 12/1996 |
| EP | 1 994 901 A1 | 11/2008 |
| FR | 2 681 525 A1 | 3/1993 |
| FR | 2693364 A1 | 1/1994 |
| FR | 2 714 591 | 7/1995 |
| FR | 2 717 675 A1 | 9/1995 |
| FR | 2722980 A1 | 2/1996 |
| FR | 2 828 398 A1 | 2/2003 |
| FR | 2 851 154 | 8/2004 |
| FR | 2 874 167 A1 | 2/2006 |
| FR | 2 884 136 A1 | 10/2006 |
| WO | WO 99/42051 A1 | 8/1999 |
| WO | WO 01/28442 | 4/2001 |
| WO | WO 02/03882 A2 | 1/2002 |
| WO | WO 02/03882 A3 | 5/2002 |
| WO | WO 02/051326 | 7/2002 |
| WO | WO 02/071960 | 9/2002 |
| WO | WO 03/045262 | 6/2003 |
| WO | WO 03/045262 A3 | 6/2003 |
| WO | WO 2004/052246 | 6/2004 |
| WO | WO 2004/073532 | 9/2004 |
| WO | WO 2004/073533 | 9/2004 |
| WO | WO 2005/037150 A1 | 4/2005 |
| WO | WO 2005/110258 A1 | 11/2005 |
| WO | WO 2008/051423 | 5/2008 |
| WO | WO 2008/051801 | 5/2008 |
| WO | WO 2008/051802 | 5/2008 |
| WO | WO 2008/051806 | 5/2008 |
| WO | WO 2008/051802 A3 | 7/2008 |
| WO | WO 2008/051806 A3 | 7/2008 |
| WO | WO 2008/051801 A3 | 8/2008 |
| WO | WO 2009/149407 | 12/2009 |
| WO | WO 2009/149407 A9 | 12/2009 |
| WO | WO 2010/028165 | 3/2010 |
| WO | WO 2010/028165 A8 | 10/2010 |

OTHER PUBLICATIONS

Dickman et al., "Comparative Mechanical Properties of Spinal Cable and Wire Fixation Systems," Spine, vol. 22, No. 6, Mar. 15, 1997, pp. 596-604.

Garner et al., "Development and Preclinical Testing of a New Tension-Band Device for the Spine: the Loop system," European Spine Journal, vol. 11 (Suppl 2), 2002 , pp. S186-S191.

Heller, "Stability of Different Wiring Techniques in Segmental Spinal Instrumentation. An Experimental Study," Archives of Orthopedic and Trauma Surgery, vol. 117, No. 1-2, Nov. 1997, pp. 96-99.

Leahy et al., "Design of Spinous Process Hooks for Flexible Fixation of the Lumbar Spine," Proceedings of the Institution of Mechanical Engineers, Part H, Journal of Engineering in Medicine, vol. 214, No. 5, Sep. 27, 2000 , pp. 479-487.

Leahy et al., "Mechanical Testing of a Flexible Fixation Device for the Lumbar Spine," Proceedings of the Institution of Mechanical Engineers, Part H: Journal of Engineering in Medicine, vol. 214, No. 5, Sep. 27, 2000 , pp. 489-495.

Minns et al., "Preliminary Design and Experimental Studies of a Novel Soft Implant for Correcting Sagittal Plane Instability in the Lumbar Spine," Spine, vol. 22, No. 16, Aug. 15, 1997, pp. 1819-1825.

Miyasaka et al., "Radiographic Analysis of Lumbar Motion in Relation to Lumbosacral Stability: Investigation of Moderate and Maximum Motion," Spine, vol. 25, No. 6, Mar. 15, 2000, pp. 732-737.

Papp et al., "An In Vitro Study of the Biomechanical Effects of Flexible Stabilization on the Lumbar Spine," Spine, vol. 22, No. 2, Jan. 15, 1997, pp. 151-155.

Shepherd et al., "Spinous Process Strength," Spine, vol. 25, No. 3, Feb. 1, 2000, pp. 319-323.

Shepherd, "Slippage of a Spinous Process Hook During Flexion in a Flexible Fixation System for the Lumbar Spine," Medical Engineering and Physics, vol. 23, No. 2, Mar. 2001, pp. 135-141.

Voydeville et al., "Ligamentoplastie Intervertebrale Avec Cale Souple dans Les Instabilites Lombaries" <<Intervertebral Ligamentoplasty with Flexible Wedge in Lumbar Instability,>>, Orthop Traumatol, vol. 2, 1992, pp. 259-264.

International Search Report and Written Opinion of PCT Application No. PCT/US2007/81822, dated May 8, 2008, 10 pages.

Frymoyer et al., "An Overview of the Incidence and Costs of Low Back Pain" Orthrop. Clin. North Am., 1991;22: 263-271.

Abbott Spine, Wallis Surgical Technique [Product Brochure], 2006; 24 pages total.

Medtronic Sofamor Danek USA, Inc., DIAM™ System Implant; 2006 [Product Brochure]; downloaded from the Internet: <http://spineinfo.ru/~files/DIAMST.pdf>, 20 pages total.

European Search Opinion of EP Patent Application No. 07863431.8, mailed Jun. 4, 2010, 5 pages total.

International Search Report and Written Opinion of PCT Application No. PCT/US2010/031615, mailed Jun. 18, 2010, 9 pages total.

International Search Report and Written Opinion of PCT Application No. PCT/US2010/031471, mailed Jul. 8, 2010, 13 pages total.

Chapter 11: Mechanical Aspects of Lumbar Spine in Musculoskeletal Biomechanics., Paul Brinckmann, Wolfgang Frobin, Gunnar Leivseth (Eds.), Georg Thieme Verlag, Stuttgart, 2002; p. 105-128.

European office action dated Feb. 4, 2011 for EP Application No. 07863431.8.

European office action dated Jun. 4, 2010 for EP Application No. 07852824.7.

European office action dated Oct. 5, 2009 for EP Application No. 07852824.7.

European search report and search opinion dated Oct. 13, 2009 for EP Application No. 07863431.8.

International search report and written opinion dated Mar. 14, 2008 for PCT/US2007/022191.

International search report and written opinion dated Mar. 24, 2008 for PCT/US2007/081835.

International search report and written opinion dated Jun. 23, 2008 for PCT/US2007/081815.

Hamblen. Symposium Dynamic stabilization of the lumbar spine. Orthopaedics today international. Mar. 2006; 9:3. orthosupersite.com/view.asp?rID=6932.

Moll, et al. Normal range of spinal mobility. Ann. Rheum. Dis. 1971; 30:381-386.

* cited by examiner

METHODS AND SYSTEMS FOR CONSTRAINT OF MULTIPLE SPINE SEGMENTS

The present application is a continuation-in-part of U.S. Patent Application No. PCT/US2007/081822 filed Oct. 18, 2007, which claims priority to U.S. Provisional Patent Application No. 60/862,085 filed Oct. 19, 2006. The present application also is a non-provisional of, and claims the benefit of U.S. Provisional Patent Application No. 61/158,892 filed Mar. 10, 2009. The entire contents of each of the above applications is incorporated herein by reference.

BACKGROUND OF THE INVENTION

1. Field of the Invention

The present invention relates generally to medical methods and apparatus. More particularly, the present invention relates to methods and devices for restricting spinal flexion in patients having back pain or other spinal conditions.

A major source of chronic low back pain is discogenic pain, also known as internal disc disruption. Patients suffering from discogenic pain tend to be young, otherwise healthy individuals who present with pain localized to the back. Discogenic pain usually occurs at the discs located at the L4-L5 or L5-S1 junctions of the spine (FIG. 1). Pain tends to be exacerbated when patients put their lumbar spines into flexion (i.e. by sitting or bending forward) and relieved when they put their lumbar spines into extension (i.e. arching backwards). Discogenic pain can be quite disabling, and for some patients, can dramatically affect their ability to work and otherwise enjoy their lives.

This pain experienced by patients with discogenic low back pain can be thought of as flexion instability, and is related to flexion instability that is manifested in other conditions. The most prevalent of these is spondylolisthesis, a spinal condition in which abnormal segmental translation is exacerbated by segmental flexion. The device described here should as such also be useful for these other spinal disorders associated with segmental flexion, for which the prevention or control of spinal segmental flexion is desired.

Current treatment alternatives for patients diagnosed with chronic discogenic pain are quite limited. Many patients follow a conservative treatment path, such as physical therapy, massage, anti-inflammatory and analgesic medications, muscle relaxants, and epidural steroid injections, but typically continue to suffer with a significant degree of pain. Other patients elect to undergo spinal fusion surgery, which commonly requires discectomy (removal of the disk) together with fusion of adjacent vertebra. Fusion is not usually recommended for discogenic pain because it is irreversible, costly, associated with high morbidity, and of questionable effectiveness. Despite its drawbacks, however, spinal fusion for discogenic pain remains common due to the lack of viable alternatives.

Recently, a less invasive and potentially more effective treatment for discogenic pain has been proposed. A spinal implant has been designed which inhibits spinal flexion while allowing substantially unrestricted spinal extension. The implant is placed over one or more adjacent pairs of spinal processes and provides an elastic restraint to the spreading apart of the spinal processes which occurs during flexion. Such devices and methods for their use are described in U.S. Patent Publication No. 2005/0216017A1, published on Sep. 29, 2005, (now U.S. Pat. No. 7,458,981) and having common inventors with the present application. The entire contents of U.S. Patent Publication No. 2005/0216017 A1 are incorporated herein by reference.

As illustrated in FIG. 2, an implant 10 as described in the '017 publication, typically comprises an upper strap component 12 and a lower strap component 14 joined by a pair of compliance members 16. The upper strap 12 is shown disposed over the top of the spinous process SP4 of L4 while the lower strap 14 is shown extending over the bottom of the spinous process SP5 of L5. The compliance member 16 will typically include an internal element, such as a spring or rubber block, which is attached to the straps 12 and 14 in such a way that the straps may be "elastically" or "compliantly" pulled apart as the spinous processes SP4 and SP5 move apart during flexion. In this way, the implant provides an elastic tension on the spinal processes which provides a force that resists flexion without substantially limiting extension of the segment. The force increases as the processes move further apart. Usually, the straps themselves will be essentially non-compliant so that the degree of elasticity or compliance may be controlled and provided solely by the compliance members 16.

Although providing significant benefits, the system illustrated in FIG. 2 is intended to treat only a single spinal segment between a pair of adjacent vertebral bodies. In some patients, it would be desirable to treat two or more successive spinal segments.

For these reasons, it would be desirable to provide improved spinal implants, implant systems, and methods for their use for limiting flexion in two or more successive spinal segments. It would be particularly desirable if the implants, systems, and methods permitted the spinous processes of three or more adjacent vertebral bodies, or two adjacent vertebral bodies and the sacrum, to be elastically coupled using a single implant structure which can constrain multiple adjacent spinal features. At least some of these objectives will be met by the inventions described hereinbelow.

2. Description of the Background Art

US 2005/0216017A1 has been described above. Other patents and published applications of interest include: U.S. Pat. Nos. 4,966,600; 5,011,494; 5,092,866; 5,116,340; 5,282,863; 5,395,374; 5,415,658; 5,415,661; 5,449,361; 5,456,722; 5,462,542; 5,496,318; 5,540,698; 5,609,634; 5,645,599; 5,725,582; 5,902,305; Re. 36,221; 5,928,232; 5,935,133; 5,964,769; 5,989,256; 6,053,921; 6,312,431; 6,364,883; 6,378,289; 6,391,030; 6,468,309; 6,436,099; 6,451,019; 6,582,433; 6,605,091; 6,626,944; 6,629,975; 6,652,527; 6,652,585; 6,656,185; 6,669,729; 6,682,533; 6,689,140; 6,712,819; 6,689,168; 6,695,852; 6,716,245; 6,761,720; 6,835,205; Published U.S. Patent Application Nos. US 2002/0151978; US 2004/0024458; US 2004/0106995; US 2004/0116927; US 2004/0117017; US 2004/0127989; US 2004/0172132; US 2005/0033435; US 2005/0049708; US 2006/0069447; Published PCT Application Nos. WO 01/28442 A1; WO 02/03882 A2; WO 02/051326 A1; WO 02/071960 A1; WO 03/045262 A1; WO 2004/052246 A1; WO 2004/073532 A1; and Published Foreign Application Nos. EP 0322334 A1; and FR 2 681 525 A1.

BRIEF SUMMARY OF THE INVENTION

The present invention provides spinal implants, implant systems, and methods for constraining spinous processes to elastically limit flexion of two or more adjacent spinal segments. As used herein, the phrase "spinal segment" is synonymous with the phrase "functional spinal unit (FSU)" and intended to mean the smallest physiological motion unit of the spine that exhibits biomechanical characteristics similar to those of the entire spine. A spinal segment or FSU consists of two adjacent vertebrae, the intervertebral disc and all adjoining ligaments between them and excludes other connecting tissues such as muscles. The three-joint complex that results is sometimes referred to as the "articular triad." Another term for the FSU is spinal motion segment. These definitions are taken from White A A, Panjabi M M. (1990), *Clinical Biomechanics of the Spine*, Philadelphia, J B Lippincott. The methods comprise placing a tether structure over the spinous processes of at least three adjacent vertebral bodies, or over the spinous processes of two adjacent vertebral bodies and a sacrum, wherein the structure elastically couples the at least two non-adjacent spinous processes or one spinous process and a non-adjacent sacrum. The spinous processes and optionally a sacrum can be interconnected and elastically coupled in a variety of ways.

In a first exemplary pattern, the tether structure elastically couples an upper spinous process to a lower spinous process, or to the sacrum, with at least one intermediate spinous process being free from coupling. In an alternative pattern, the tether structure elastically couples an upper spinous process and a lower spinous process or sacrum, as well as the at least one intermediate spinous process. The spinous processes and optionally the sacrum may be elastically coupled by a single contiguous tether structure, or in other embodiments may be elastically connected by two or more contiguous tether structures. In the case of two or more contiguous tether structures, the tether structures may further be interconnected, coupled, or linked in order to provide desired elastic restraint characteristics. The spinous processes being connected will typically be in the lumbar region, most typically being at the lower levels of the lumbar, and even more particularly being at L3, L4, L5 and the sacrum. In most instances, the spinous processes, and optionally the sacrum, are elastically coupled to inhibit flexion with the spaces between the adjacent vertebral bodies being free from structure which would substantially limit or inhibit extension of the spinal segments being treated. A first portion and a second portion of the tether structure may extend between the upper spinous process and the lower spinous process or the sacrum. The first and second portions of the tether structure may be disposed symmetrically on opposite sides of the spinous processes and they also may be parallel to one another.

In another aspect of the present invention, a spinal implant comprises a contiguous tether structure adapted to circumscribe at least two non-adjacent spinous processes, or in other instances, to an anchor location on the sacrum and one non-adjacent spinous process. At least a portion of the tether structure will provide an elastic resistance to elongation in response to an elongation force which results from flexion of the spinal segments between the non-adjacent spinous processes and/or between the one non-adjacent spinous process and the sacrum. The tether structure limits flexion therebetween without substantially limiting extension therebetween. A first portion and a second portion of the tether structure may extend between the non-adjacent spinous processes or between the one non-adjacent spinous process and the sacrum. The first and second portions of the tether structure may be disposed symmetrically on opposite sides of the spinous processes and they also may be parallel to one another. Often, the implant will include at least two compliance members positioned as part of the tether structure such that they will lie symmetrically on opposite sides of the spinous processes when implanted. In still other embodiments, the contiguous tether structures will include at least four such compliance members. The compliance members will typically be coupled to non-compliant and/or cable components of the tether structure so that it is the compliance members which provide most or all of the compliance or elasticity in the implants. Exemplary compliance structures are illustrated in U.S. Patent Publication No. 2005/02161017 A1 (now U.S. Pat. No. 7,458,981).

In some embodiments, the contiguous tether structure will be continuous so that the structure forms a loop which may be placed over the non-adjacent spinous processes. Such continuous "loop" tether structures will usually be maintained on the spinous processes by friction and interference fit, but in some cases could be modified to permit further attachment by stapling, welding, gluing, suturing, or the like. In other embodiments, the contiguous tether structure will be discontinuous and will have two ends which are adapted for anchoring for direct attachment to the bone. Such discontinuous tether structures will be suitable for anchoring in the sacrum.

In a third aspect of the present invention, systems comprising a spinal implant as generally described above further include at least one additional contiguous tether structure. The additional tether structure will usually be adapted to circumscribe two adjacent or non-adjacent spinous processes or a sacrum. The additional contiguous tether structures may be continuous so that they can be looped over the spinous processes, or in other instances may be discontinuous and have two ends adapted for anchoring directly in the bone. The additional contiguous tether structure may be interconnected with the primary tether structure but will frequently be formed separately.

In still another aspect of the present invention, a method for constraining spinous processes to elastically limit flexion of two or more adjacent spinal segments comprises placing a first tether structure over a superior spinous process and an inferior spinous process of a first spinal segment. The first tether structure elastically couples the superior spinous process and the inferior spinous process so as to limit flexion therebetween without substantially limiting extension thereof. A first portion of the first tether structure extends between the superior spinous process and the inferior spinous process of the first spinal segment, and a second portion of the first tether structure extends between the superior spinous process and the inferior spinous process of the first spinal segment. The first and the second portions are disposed symmetrically on opposite sides of the spinous processes, and they are substantially parallel to one another. The method also comprises placing a second tether structure over a superior spinous process and an inferior spinous process or a sacrum of a second spinal segment. The second tether structure elastically couples the superior spinous process and the inferior spinous process or the sacrum of the second spinal segment so as to limit flexion therebetween without substantially limiting extension thereof. A first portion of the second tether structure extends between the superior spinous process and the inferior spinous process or the sacrum of the second spinal segment, and a second portion of the second tether structure extends between the superior spinous process and the inferior spinous process or the sacrum of the second spinal segment. The first and the second portions are disposed symmetrically on opposite sides of the spinous processes, and they are substantially parallel to one another. The first spinal segment is adjacent and superior to the second spinal segment, and one of the first or second tether structures is positioned anteriorly relative to the other tether structure.

In some embodiments, the tether structure may be disposed around a first surface of the a spinous process and a second tether structure may be positioned around a second surface of the spinous process, opposite the first surface. The two tethers may be positioned on the spinous process such that one tether is anteriorly disposed on the spinous process relative to the other tether structure.

In other embodiments, the tether structure may have a first compliance member with a first elasticity and a second compliance member with a second elasticity different than the first elasticity. The tether structure may also comprise a first pair of compliance members and a second pair of compliance members. Each of the first pair may have a first elasticity and each of the second pair may have a second elasticity. The first elasticity may be the same or different than the second elasticity. The first pair of compliance members may be superior to the second pair of compliance members.

In preferred embodiments, the tether structure inhibits or limits flexion of a spinal segment without substantially limiting extension therebetween. Thus, in some embodiments, the tether structure may have an elastic stiffness in compression below 3 N/mm and in other embodiments the elastic stiffness in compression may be below 0.5 N/mm.

In still other embodiments, the tether structure may be positioned over an upper spinous process, a lower spinous process and an intermediate spinous process disposed therebetween. The tether structure may comprise a first loop encircling the lower spinous process and the intermediate spinous process so as to substantially prevent flexion therebetween, and the tether structure may also comprise a second loop superior to the first loop. The second loop may have one or more compliance members and may be disposed over the upper spinous process and coupled with the first loop so as to provide a force resistant to flexion of a superior spinal segment relative to the inferior spinal segment.

These and other embodiments are described in further detail in the following description related to the appended drawing figures.

DETAILED DESCRIPTION OF THE INVENTION

The present invention provides methods, devices, and systems for constraining the flexion of two or more adjacent spinal segments by elastically restraining two or more spinous processes or at least one spinous process and an anchor region on a sacrum. Such restraint is achieved using a tether structure which spans at least three spinous processes or a pair of spinous processes and the sacrum (more specifically, the spinous processes on L4 and L5 as well as an anchor region on the sacrum). The tethers used will typically be in the form of a contiguous tether structure. By "contiguous" it means that the tether may comprise one or more elongate component(s), such as strap(s), cable(s), ribbon(s), or the like, which may be constructed or modified to provide for a desired elastic coupling of one or more spinous processes and optionally an anchor location on the sacrum. Alternatively, the "contiguous" tether structures may comprise a plurality of components, such as the straps, bands, cables, or the like, as mentioned above, together with compliance structures which provide for the desired elastic coupling. In the latter case, the straps, etc., will typically be non-compliant, effecting little or no elongation in response to tension, while the compliance members will provide the desired level of elastically coupling. Combinations of compliant elongate components and separate compliance members will also be possible.

The contiguous tether structures may be continuous or discontinuous. The "continuous" contiguous tether structures will typically be formed into a loop so that the loop may be placed over a pair of spinous processes, typically non-adjacent spinous processes separated by at least one intermediate spinous process. The "discontinuous" contiguous tether structures, in contrast, will have at least two free ends adapted with anchor structures for anchoring to bone, typically to anchor regions on a sacrum.

Figure 1:
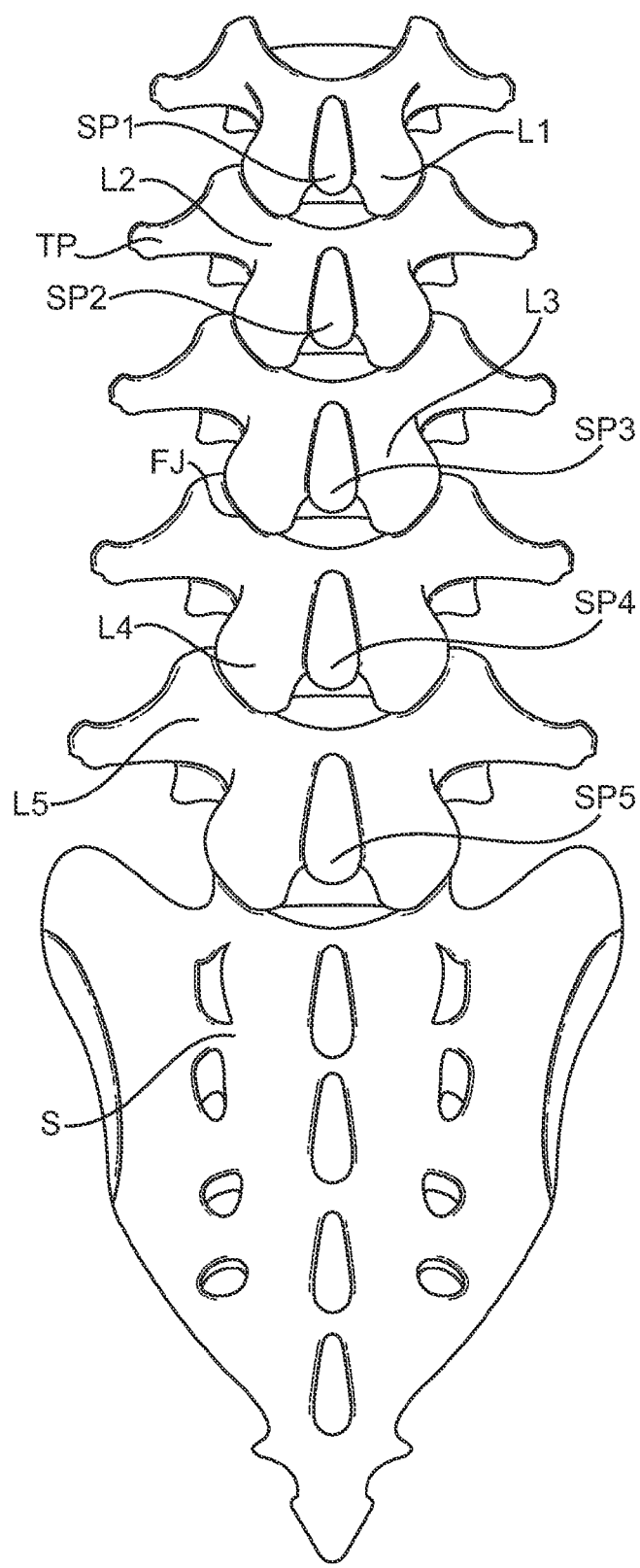
FIG. 1 is a schematic diagram illustrating the lumbar region of the spine including the spinous processes (SP), facet joints (FJ), lamina (L), transverse processes (TP), and sacrum (S).
Figure 2:
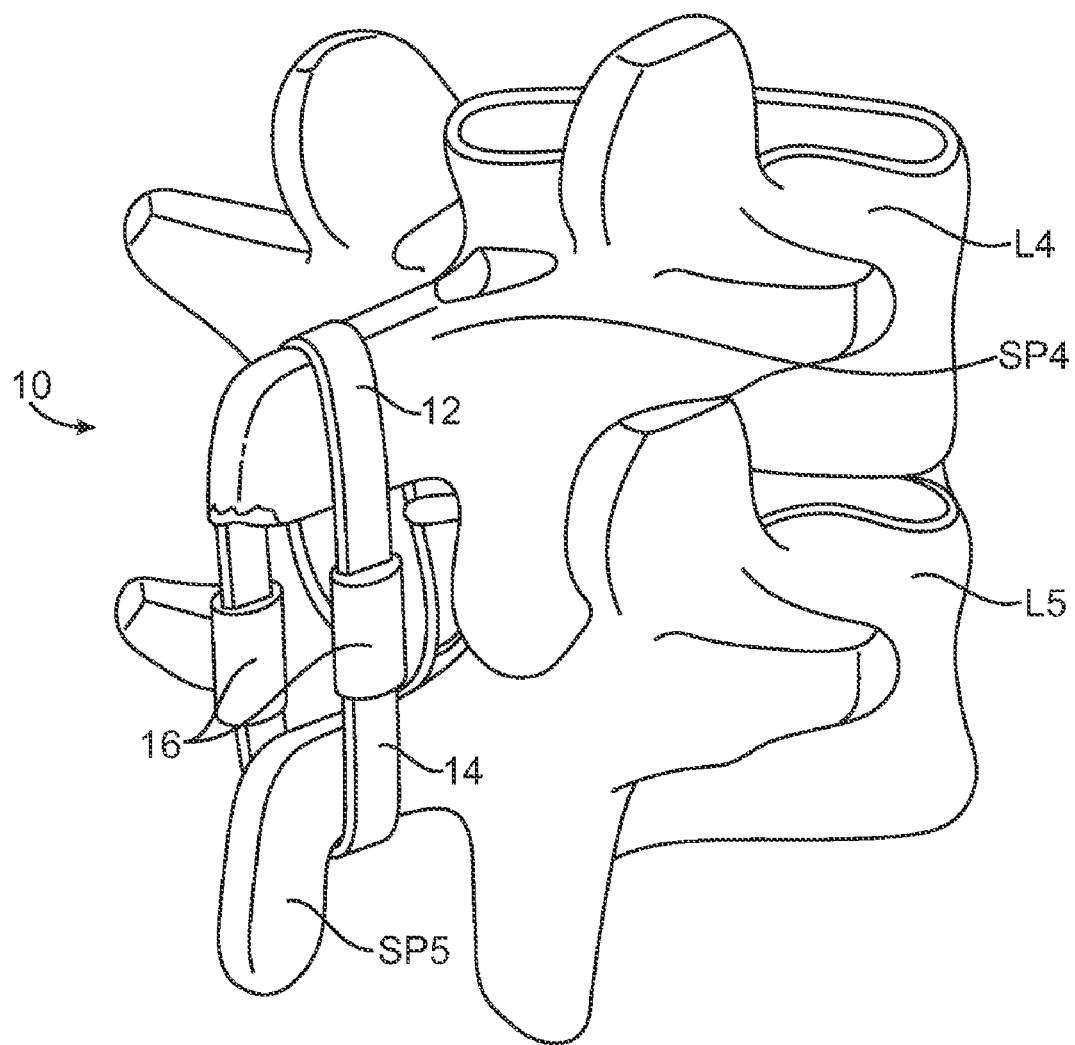
FIG. 2 illustrates a spinal implant of the type described in US 2005/0216017A1.
Figure 3:
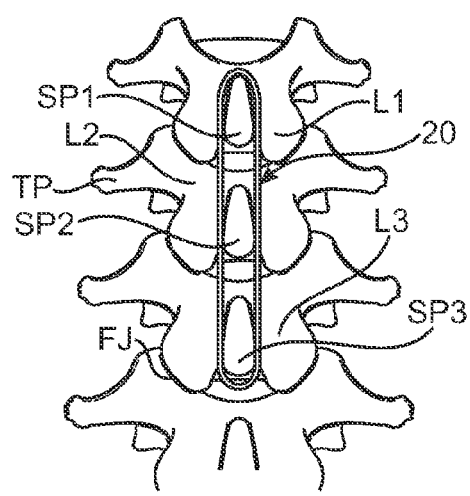
FIG. 3 illustrates a contiguous tether structure constructed in accordance with the principles of the present invention and adapted for placement over three adjacent spinous processes.

Referring now to FIG. 3, a first exemplary continuous tether structure 20 is shown circumscribing the spinous processes SP1-SP3 on the L1-L3 vertebral bodies. The tether structure 20 may be a simple band, strap, or cable which is formed into a continuous loop, where at least a portion of the structure provides a desired elasticity to inhibit flexion of the spinal segments between L1 and L2 and L2 and L3 in a controlled manner. Elasticity may be provided through use of an elastomeric material, inclusion of spring-like or elastic regions in an otherwise inelastic or non-compliant structure, or the like.

Figure 4:
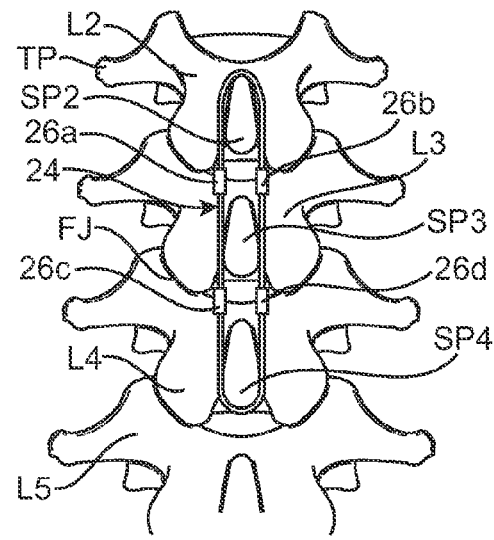
FIG. 4 illustrates a contiguous tether structure similar to that shown in FIG. 3 which further includes four symmetrically placed compliance structures.

Referring now to FIG. 4, a second exemplary continuous tether structure 24 is similar to tether 20, except that it is provided with separate compliance structures 26a-26d arranged symmetrically on opposite sides of the "ridge" of spinous processes. The tether structure 24 is shown placed on the spinous processes SP2-SP4 on vertebral bodies L2-L4, it will be appreciated that tether structures 20 and 24 could be placed on any three contiguous spinous processes, typically in the lumbar region. Various combinations of elasticities may be used amongst the four compliance members 26a-26d. For example, all four compliance members may have the same elasticity. Alternatively, all four compliance members may have an elasticity different from one another. In some embodiments, the two superior compliance members 26a, 26b may have a first elasticity and the two inferior compliance members 26c, 26d may have a second elasticity different than the first. This allows the resistance to flexion to be varied at different levels of the spinal segment. In still other embodiments, at one motion segment level, the elasticity of a left compliance member 26a may be different than the right compliance member 26b. One of skill in the art will appreciate that any combination of elasticities may be employed in a tether structure having multiple compliance members. This applies to any of the embodiments disclosed herein having multiple compliance members.

The continuous tether structures of the present invention may be formed in multiple interconnected loops, as shown, for example, in FIGS. 5-8. The multiple loops will usually include an outer or peripheral loop which encircles or otherwise engages at least three or more adjacent spinous processes. One or more inner loops may also be provided to engage or encircle one, two, or possibly more of "intermediate" spinous processes within the group which is being restrained.

Figure 5:
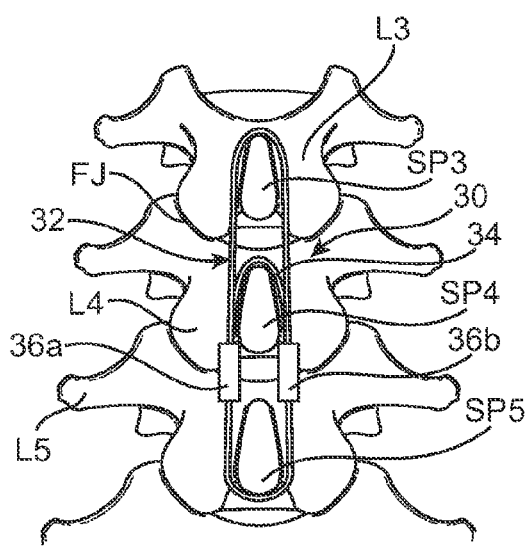
FIG. 5 illustrates a contiguous tether structure constructed in accordance with the principles of the present invention which is adapted for placement over three adjacent spinous processes and which further includes an intermediate loop segment for engaging the intermediate spinous process.

For example, in FIG. 5, a continuous tether structure 30 includes an outer loop 32 which encircles three adjacent spinous processes, shown as SP3-SP5 on vertebral bodies L3-L5. An inner loop 34 is provided which encircles only SP4 and SP5. The upper portions of the two loops 32 and 34 are both connected in compliance members 36a and 36b. The compliance members may be configured to apply a generally equal elastic tensioning to the upper loop portions as the spinal segments undergo flexion. Alternatively, the compliance members 36a and 36b could be configured to provide different elastic tensioning forces to the upper segments of loops 32 and 34, respectively.

Figure 6:
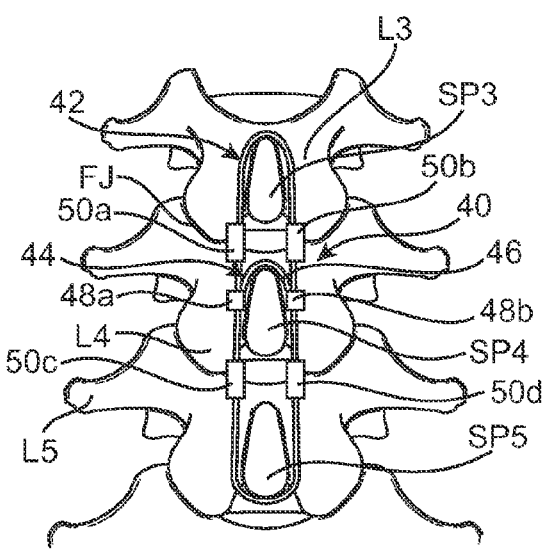
FIG. 6 illustrates a contiguous tether structure similar to that shown in FIG. 5, where the intermediate loop structure is adjustably attached to the main tether structure.

Continuous tether structure 40, as shown in FIG. 6, also comprises an outer loop 42 (shown to encircle SP3-SP5) and an inner loop 44 (shown to encircle SP4 and SP5 only), similar to the tether structure 30 of FIG. 5. An upper loop portion 46, however, is shown attached to sliding attachment members 48a and 48b, which attachment members allow the upper loop structure 46 to be tightened or "cinched" over the top of SP4. The tether structure 40 is also shown with four symmetrically placed compliance members 50a-50d, but it will be appreciated that the tether structure could include only two or even no compliance members, while retaining the adjustably placed upper loop structure 46. As discussed above, any combination of elasticities may be used amongst the compliance members.

Figure 7:
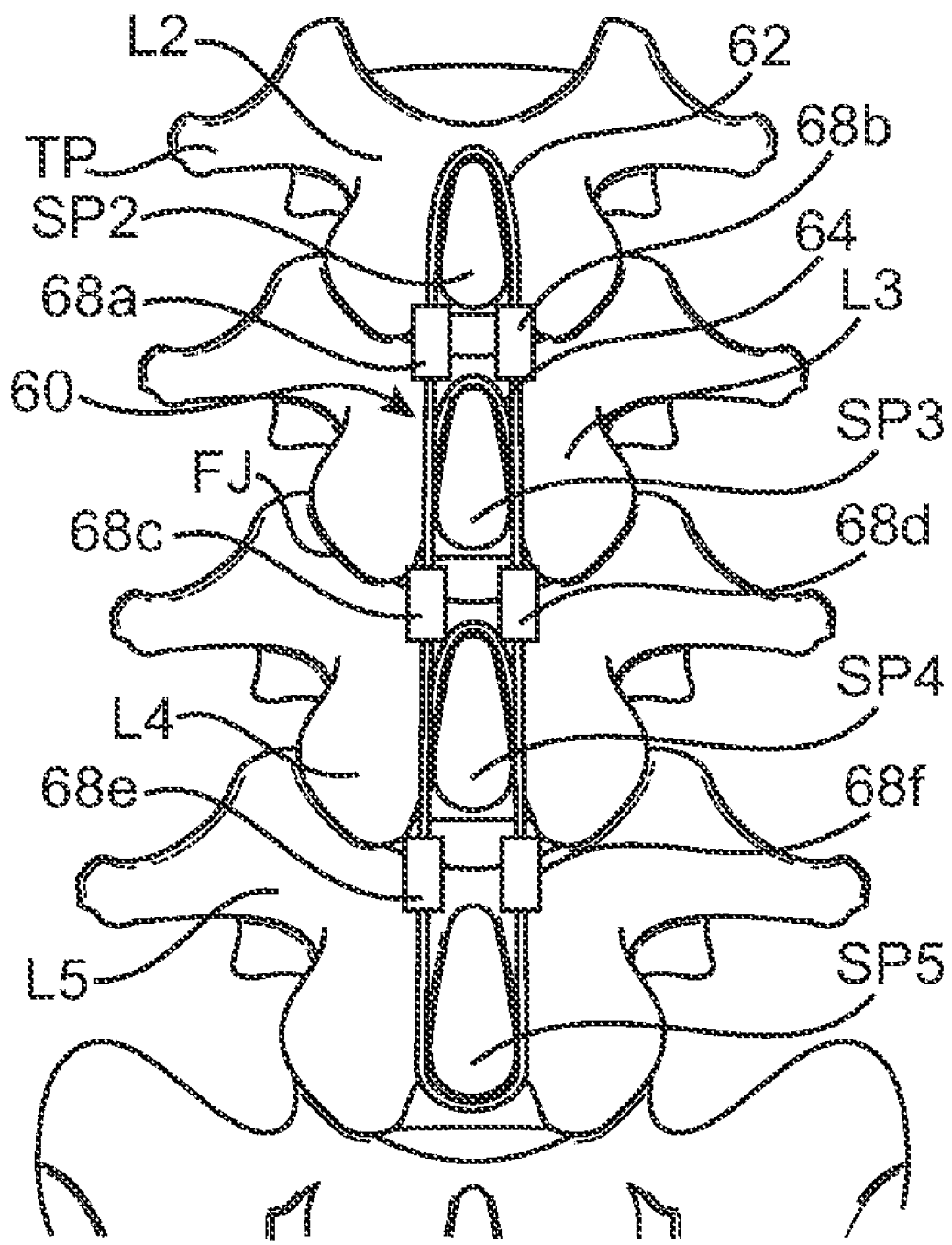
FIG. 7 illustrates a contiguous tether structure constructed in accordance with the principles of the present invention and adapted for placement over four adjacent spinous processes including two intermediate loop structures and six symmetrically placed compliance members.

A more complex continuous tether structure 60 including one external loop and two internal loops is illustrated in FIG. 7. The external loop is configured to circumscribe four adjacent spinous processes (SP2-SP4) while the first internal loop defined by loop segment 64 extends over SP3 and a second internal loop segment 66 extends over SP4. Six compliance members 68a-68f are provided symmetrically on opposite sides of the spinous processes, and the ends of the first upper loop segment 64 are connected to compliance members 68c and 68d, respectively, while the ends of the second loop segment 66 are connected to compliance members 68e and 68f, respectively. It will be appreciated that the use of six compliance members and the two intermediate loop segments allows the tension on each of the spinous processes to be independently adjusted to some extent. The overall compliance and elastic force applied to the spinal segments, however, will depend on the cumulative value of the elastic forces provided by all of the compliance members. Thus, elasticity may be varied amongst the compliance members, as previously discussed above.

Figures 8, 8A:
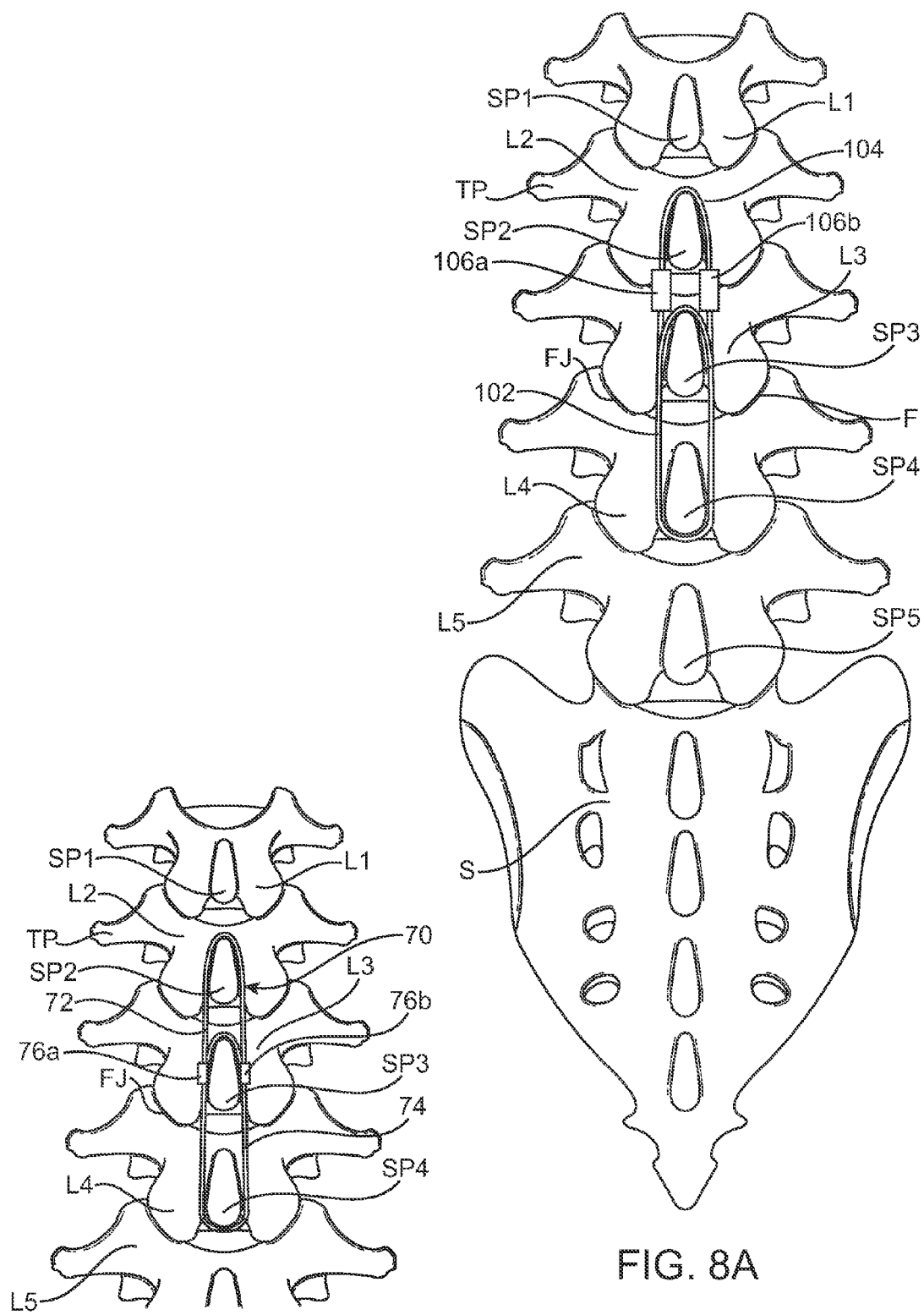
FIG. 8 illustrates yet another contiguous tether structure constructed in accordance with the principles of the present invention comprising two loop segments joined together by connectors adjacent an intermediate spinous process.
FIG. 8A illustrates another embodiment of a tether structure constructed in accordance with the principles of the present invention comprising two loop segments.

A multiple loop tether structure 70 having a more simple configuration is shown in FIG. 8. An upper loop 72 is adapted to circumscribe a pair of adjacent spinous processes (shown as SP2 and SP3) while a lower loop is adapted to circumscribe an overlapping pair of spinous processes (shown as SP3 and SP4). The two loops are joined by connector components 76a and 76b which may be simple clips or crimps to hold the loops 64 and 66 together (in which case the loops would likely be elastic or partially elastic to allow for controlled flexion of the spinal segments) or could be compliance members which provide for controlled, elastic movement of the upper loop 72 relative to the lower loop 74. In the latter case, the loops would likely be non-compliant.

FIG. 8A illustrates another embodiment similar to that of FIG. 8, except here the tether structure is coupled to two adjacent spinous processes at a first level of the spinal segment and another portion of the tether structure having compliance members is then coupled to a superior spinous process so that flexion is restricted in the suprajacent segment. This may be used, for example, when the spinal segment is fused. In FIG. 8A, a first part of the tether structure consists of a tether 102 circumscribing two adjacent spinous processes SP3-SP4. The tether 102 is disposed around a superior surface of a superior spinous process SP3 and also around an inferior surface of an inferior spinous process SP4. A fusion according to methods known in the art has been performed to fuse L3-L4 together at, or across the level designated by F and therefore tether 102 will often be substantially inelastic in order to prevent flexion between L3-L4 thereby facilitating the fusion F, although some micromotion is still permitted. The tether structure also has a second tether 104 disposed around a superior surface of a superior spinous process SP2 superior to the fused region. The ends of the second tether 104 are coupled with the first part of the tether structure 102, or in alternative embodiments, the ends of the second tether 104 are continuous forming a closed loop and thus are disposed under the inferior surface of SP3. Compliance members 106a, 106b provide a force resistant to flexion of the L2-L3 motion segment supradjacent to the fused region F. This helps to more evenly distribute and possibly lessen loading applied to the fused region, to the level superior to the fused region, and to tethers 102 and 104. The tether structure may also help to reduce excessive motion. Additional details on the use of a tether structure concomitantly with fusion are disclosed in U.S. Provisional Patent Application Nos. 61/158,892 and 61/158,886, both filed on Mar. 10, 2009, and both of which the entire contents are incorporated herein by reference.

Figure 9:
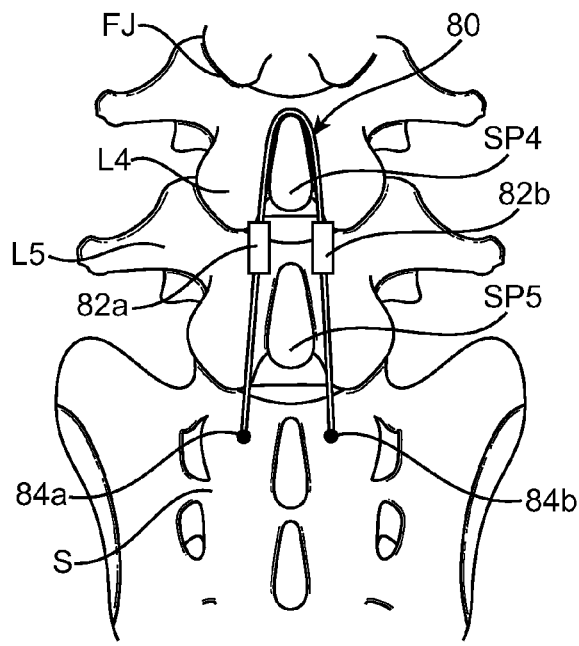
FIG. 9 illustrates a contiguous tether structure constructed in accordance with the principles of the present invention and having a discontinuous structure with two ends adapted for anchoring in the sacrum.
Figure 10:
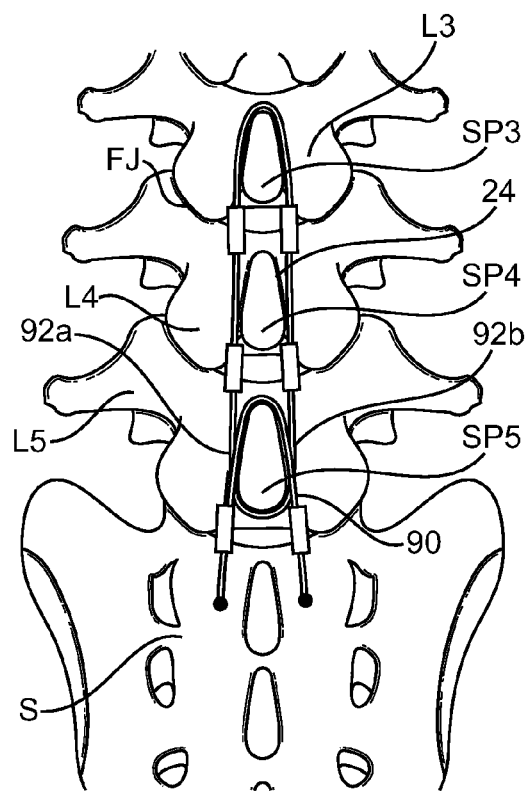
FIG. 10 illustrates a system constructed in accordance with the principles of the present invention and including two contiguous tether structures which may be used simultaneously.

The contiguous tether structures of the present invention will not always have a continuous structure. As shown in FIGS. 9 and 10, the tether structures may also have a discontinuous geometry including at least two ends adapted to anchor to bone, typically to a surface of the sacrum which generally lacks structure for attaching the lower end of a loop. As shown in FIG. 9, an exemplary discontinuous tether structure 80 comprises a U-shaped tether or band structure including compliance members 82a and 82b. A pair of anchor structures 84a and 84b are provided on two ends of the tether structure 80 and are adapted to be anchored into the face of the sacrum S, as illustrated. In this way, the tether structure 80 can provide for controlled elastic restraint of the spinal segments between SP4 and SP5 and between SP5 and the sacrum.

Additional details on sacral attachment may be found in U.S. Provisional Patent Application No. 61/149,224, filed Feb. 2, 2009, and U.S. patent application Ser. No. 11/827,980, filed Jul. 13, 2007. The entire contents of each of these applications is incorporated herein by reference.

FIG. 10 illustrates a system including a tether structure 24, generally as described with reference to FIG. 4 above, and a second tether structure 90 which is similar to tether structure 80, except that it is adapted only to extend around a single spinous process (SP5) and to be anchored into the sacrum S. Attachment may be provided in a variety of ways as described in copending application Ser. Nos. 11/827,980 and 61/149,224, both previously incorporated herein by reference. The second tether structure may be attached using a dowel implanted in the sacrum, using alar screws, using superior articular facet screws, using toggle anchors (T-tags) placed in holes formed in a superior articular facet of S1, using hooks attached to the dorsal S1 foramen, or the like. The tether structure 24 and tether structure 90 could be deployed without any interconnection, as generally shown in FIG. 10. Often, however, it might be desirable to interconnect the tether structures at their crossover points 92a, 92b, generally adjacent to the two sides of SP5. The attachment could be accomplished using a crimp structure (not shown) or by otherwise tying, welding, or fusing the tether structures together.

Figure 11:
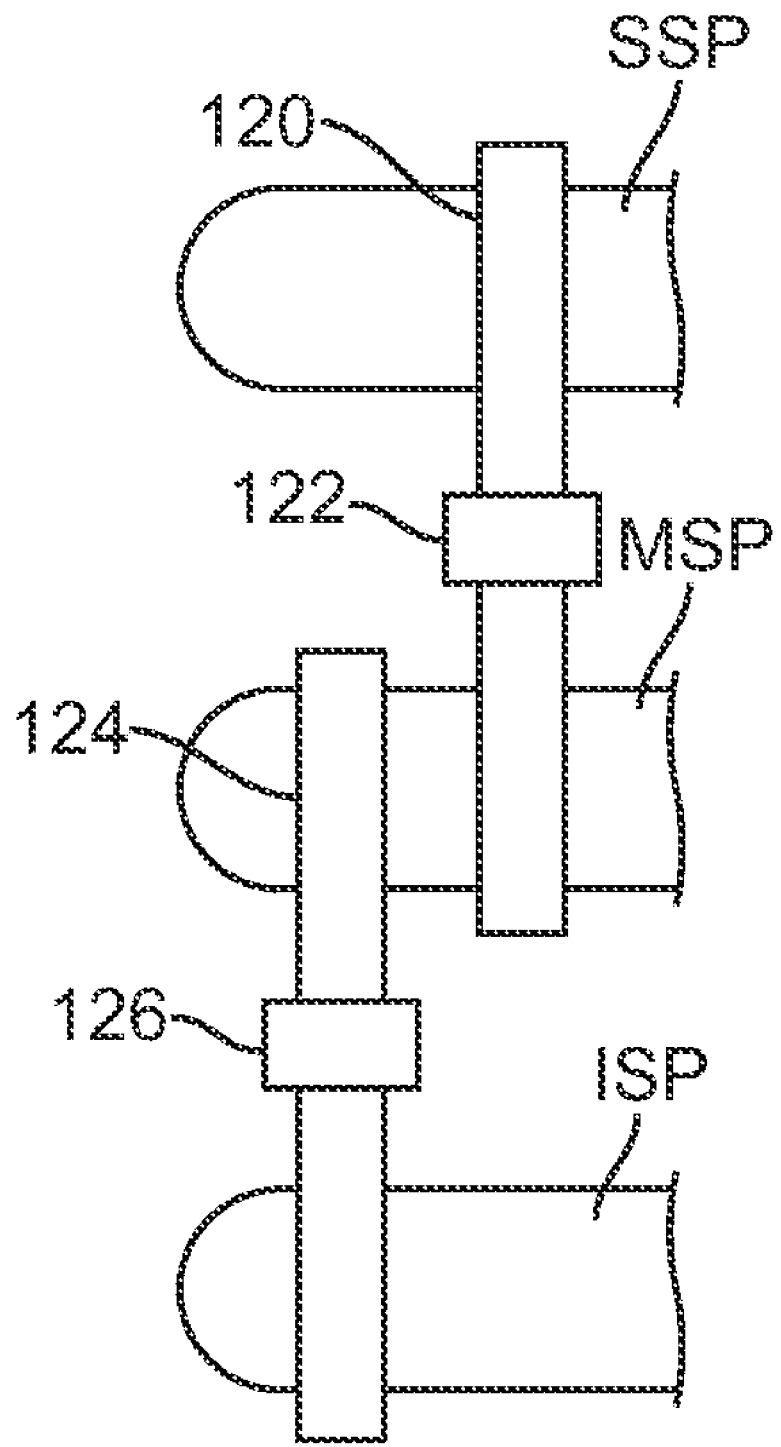
FIG. 11 illustrates a sagittal view of tethers applied to adjacent spinous processes.

FIG. 11 illustrates a sagittal view of a spinal segment and shows the positioning of tethers around the spinous processes. In FIG. 11, a first tether structure 120 having two compliance members 122 (only one visible in this view) is disposed over a superior surface of a superior spinous process SSP and also is disposed under an inferior surface of an intermediate spinous process MSP. A second tether structure 124 having two compliance members 126 (only one visible in this view) is disposed over a superior surface of the intermediate spinous process MSP and under an inferior surface of the inferior spinous process ISP. In embodiments where multiple tethers are coupled to a spinous process, such as in SP5 in FIG. 10, the first tether may be coupled to the spinous process and it is often advanced in the anterior direction in order to allow room for the second tether which will be slightly posterior to the first tether. FIG. 11 shows the first tether structure 120 anterior to the second tether structure 124 on the intermediate spinous process MSP. While this embodiment shows a slight gap between the two tethers, the two tethers may also be pushed against one another so there is no gap, or in some embodiments the two tethers may slightly overlap one another.

In each of the embodiments disclosed herein, the tether structure limits flexion of a spinal segment. Additionally, because the tether structure is flexible and has a low elastic stiffness in compression, it does not substantially limit extension of the spinal segment. Any of the embodiments may utilize tether structures that have an elastic stiffness in compression below 3 Newtons per millimeter (N/mm). In some embodiments the elastic stiffness in compression may be below 0.5 N/mm.

It will be appreciated that numerous other combinations of continuous tether structures and discontinuous tether structures could be provided in order to effect the controlled application of elastic restraint on adjacent spinal segments in the lumbar region of the spine. Thus, the examples set forth above are not meant to be limiting on the breadth of the invention as set forth in the following claims.

What is claimed is:

1. A method for constraining spinous processes to elastically limit flexion of two or more adjacent spinal segments, said method comprising:

placing a first tether structure over a superior spinous process and an inferior spinous process of a first spinal segment, wherein the first tether structure elastically couples the superior spinous process and the inferior spinous process so as to limit flexion therebetween without substantially limiting extension thereof, wherein a first portion of the first tether structure extends between the superior spinous process and the inferior spinous process of the first spinal segment, and a second portion of the first tether structure extends between the superior spinous process and the inferior spinous process of the first spinal segment, the first and the second portions disposed symmetrically on opposite sides of the spinous processes, and substantially parallel to one another; and placing a second tether structure over a superior spinous process and an inferior spinous process or a sacrum of a second spinal segment, the first spinal segment being adjacent and superior to the second spinal segment, wherein the second tether structure elastically couples the superior spinous process and the inferior spinous process or the sacrum of the second spinal segment so as to limit flexion therebetween without substantially limiting extension thereof, wherein a first portion of the second tether structure extends between the superior spinous process and the inferior spinous process or the sacrum of the second spinal segment, and a second portion of the second tether structure extends between the superior spinous process and the inferior spinous process or the sacrum of the second spinal segment, the first and the second portions disposed symmetrically on opposite sides of the spinous processes, and substantially parallel to one another, and wherein one of the first or the second tether structures is positioned anteriorly relative to the other tether structure.

2. A method as in claim 1, wherein the first tether structure or the second tether structure comprises a contiguous tether structure.

3. A method as in claim 1, wherein the inferior spinous process of the first spinal segment comprises an intermediate spinous process, and the first tether structure is disposed around a first surface of the intermediate spinous process, and wherein the superior spinous process of the second spinal segment comprises the intermediate spinous process, the method further comprises positioning the second tether structure around a second surface of the intermediate spinous process, wherein the second surface is opposite the first surface, and wherein the second tether positioned on the intermediate spinous process such that one tether is anteriorly disposed relative to the other tether structure.

4. A method as in claim 1, wherein one of the spinous processes in the first or the second spinal segment is disposed on an L4 or L5 vertebrae, or disposed on the sacrum.

5. A method as in claim 1, wherein spaces between adjacent spinous processes are free from structure which would inhibit extension therebetween.

6. A method as in claim 1, wherein the first or the second tether structure comprises one or more band elements in series with one or more compliance members, wherein the one or more compliance members provide the elasticity to limit the flexion.

7. A method as in claim 1, wherein the first or the second tether structure comprises at least two compliance members, the method further comprising positioning the compliance members symmetrically to lie on opposite sides of the spinous processes, and wherein the at least two compliance members provide the elasticity to limit the flexion.

8. A method as in claim 1, wherein the first or the second tether structure provides an elastic stiffness in compression below 3 N/mm.

9. A method as in claim 8, wherein the elastic stiffness in compression is below 0.5 N/mm.

* * * * *